United States Patent

Stoss et al.

[11] 4,056,526
[45] Nov. 1, 1977

[54] BENZO(b)THIOPHENE DERIVATIVES

[75] Inventors: Peter Johannes Stoss, Wildtal; Manfred Franz Reinhold Herrmann, Gundelfingen; Gerhard Satzinger, Denzlingen, all of Germany

[73] Assignee: Warner-Lambert Company, Morris Plains, N.J.

[21] Appl. No.: 691,109

[22] Filed: May 28, 1976

Related U.S. Application Data

[62] Division of Ser. No. 566,469, April 9, 1975, Pat. No. 3,971,814, which is a division of Ser. No. 419,305, Nov. 27, 1973, Pat. No. 3,907,826.

[30] Foreign Application Priority Data

Nov. 27, 1972  Germany ............................ 2225803

[51] Int. Cl.$^2$ ......................................... C07D 413/02
[52] U.S. Cl. .................................................. 544/146
[58] Field of Search ................................. 260/247.1 P

[56] References Cited

U.S. PATENT DOCUMENTS

| | | | |
|---|---|---|---|
| 3,745,175 | 7/1973 | Thominey | 260/247.1 P |
| 3,907,826 | 9/1975 | Stoss et al. | 260/247.1 P |
| 3,971,814 | 7/1976 | Stoss et al. | 260/330 S |

OTHER PUBLICATIONS

Stoss et al., "Chem. Abstracts", vol. 81 (1974) No. 49568u.

Primary Examiner—Henry R. Jiles
Assistant Examiner—R. W. Ramsuer
Attorney, Agent, or Firm—Albert H. Graddis; Frank S. Chow; George M. Yahwak

[57] ABSTRACT

The present invention relates to novel benzo(b)thiophene derivatives of the general formula:

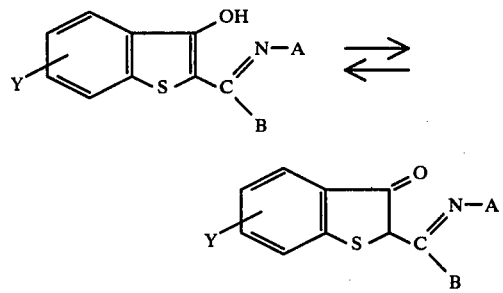

wherein Y represents a hydrogen or halogen atom; A represents a hydrogen atom or a phenyl group which may be substituted with a halogen atom or a lower alkoxy group; B represents a radical of the formula OR' or NR$^2$R$^3$, wherein R' is an alkyl radical of 1 to 5 carbons which may be substituted with hydroxy, lower alkoxy, phenyl or phenoxy groups or a cycloalkyl or phenyl group which may be substituted by lower alkoxy or halogen atoms; R$^2$ and R$^3$, which may be identical or different, represent, if identical, hydrogen, alkyl radicals of 1 to 5 carbon atoms which may be substituted by hydroxy, lower alkoxy, phenoxy, di-lower alkylamino, or phenyl groups; or, if R$^2$ is hydrogen, R$^3$ represents either a hydroxyl or an amino group which may be substituted by lower alkyl, dialkyl, alkylidene, phenyl or acyl groups or a lower alkyl group which may be substituted by hydroxy, lower alkoxy, phenoxy, dialkylamino, pyrrolidino, piperidino or morpholino groups; R$^3$ further is a cycloalkyl or phenyl group, which may be substituted by a halogen or a lower alkoxy radical; or R$^2$ and R$^3$ together with the nitrogen atom to which they are attached, may form an aziridine, pyrrolidine, piperidine, morpholine or piperazine ring which may be substituted by lower alkyl, hydroxyalkyl, phenylalkyl, phenyl or acetyl groups; or A and B together with the C═N group may form a 5, 6, or 7-membered heterocyclic ring.

4 Claims, No Drawings

BENZO(b)THIOPHENE DERIVATIVES

This is a division of application Ser. No. 566,469 filed Apr. 9, 1975, now U.S. Pat. No. 3,971,814 which in turn is a divisional of U.S. Ser. No. 419,305, filed Nov. 22, 1973, now U.S. Pat. No. 3,907,826.

The present invention further relates to the processes for the preparation of these derivatives and to the salts of these compounds with physiologically acceptable inorganic and organic acids such as hydrochloric acid, sulfuric acid, phosphoric acid, fumaric acid, oxalic acid, citric acid, etc., and the quaternary ammonium compounds.

Among the known analgesic, antipyretic, and anti-inflammatory preparations in wide use today are phenylbutazone, azapropazone, acetylsalicylic acid and indomethacin. Individually, however, each of these preparations is not efficient as an analgesic, antipyretic and anti-inflammatory. Phenylbutazone, for example, is highly effective as an anti-inflammatory, but shows little or no antipyretic properties.

It is the object of this invention to disclose a broad group of novel chemical compounds which show concurrent analgesic, antipyretic, and anti-inflammatory characteristics.

In detail, the compounds of the present invention are marked by the fact that they are prepared according to the following procedures:

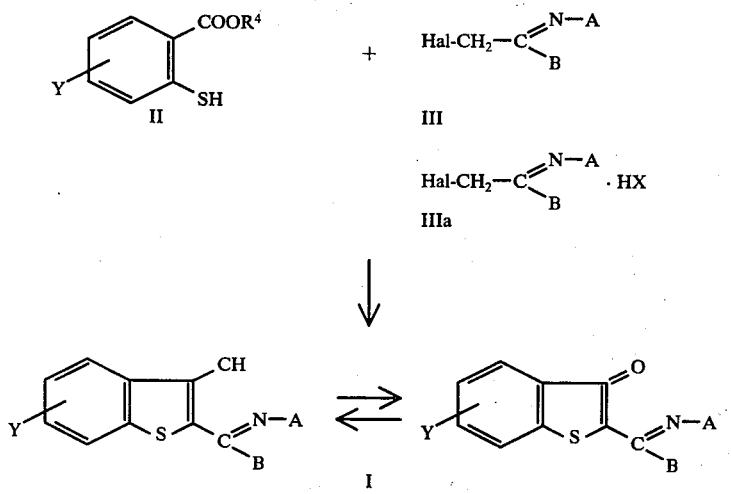

In the above procedure a thiosalicylic acid of the general formula II, in which $R_4$ represents hydrogen or a lower alkyl group, and Y represents a halogen or hydrogen, is transformed into the corresponding benzo(b)thiophene isomeric derivatives of formula I by reaction with the imidates or amidines of the general formula III, or with the salts thereof as shown by the general formula III a. In formulas I, III and III a, A represents a hydrogen atom or a phenyl group which may be substituted with a halogen atom or a lower alkoxy group; B represents a radical of the formula OR' or $NR^2R^3$, wherein R' is an alkyl radical of 1 to 5 carbons which may be substituted with hydroxy, lower alkoxy, phenyl or phenoxy groups or a cycloalkyl or phenyl group, which may be substituted by lower alkoxy or halogen atoms; $R^2$ and $R^3$, which may be identical or different, represent, if identical, hydrogen, alkyl radicals of 1 to 5 carbon atoms which may be substituted by hydroxy, lower alkoxy, phenoxy, diloweralkylamino, or phenyl groups; or, if $R^2$ is hydrogen, $R^3$ represents either a hydroxyl or an amino group which may be substituted by lower alkyl, dialkyl, alkylidene, phenyl or acyl groups or a lower alkyl group which may be substituted by hydroxy, lower alkoxy, phenoxy, dialkylamino, pyrrolidino, piperidino, or morpholino groups; $R^3$ further is a cycloalkyl or phenyl group which may be substituted by a halogen or a lower alkoxy radical; or $R^2$ and $R^3$ together with the nitrogen atom to which they are attached may form an aziridine, pyrrolidine, piperidine, morpholine or piperazine ring which may be substituted by lower alkyl, hydroxyalkyl, phenylalkyl, phenyl or acetyl groups; or A and B together with the C=N group may form a 5, 6, or 7-membered heterocyclic ring. X represents the anion of an inorganic or organic acid.

In a preferred group of compounds according to formula I, Y is hydrogen or chloro; A is hydrogen, phenyl, methoxyphenyl, chlorophenyl; B is a radical of the formula OR' or $NR^2R^3$ wherein R' is an alkyl radical of 1 to 5 carbon atoms which may be substituted by hydroxy, lower alkoxy or phenoxy groups or a cyclohexyl, phenyl, methoxyphenyl or chlorophenyl radical; $R^2$ and $R^3$, which may be identical or different, represent, if identical, hydrogen, alkyl radicals of 1 to 5 carbon atoms which may be substituted by hydroxy, lower alkoxy, phenoxy, dilower alkylamino, or phenyl groups; or, if $R^2$ is hydrogen, $R^3$ represents either a hydroxyl or an amino group which may be substituted by lower alkyl, diloweralkyl, alkylidene, phenyl, formyl, lower alkanoyl, benzoyl, pyridyl-carbonyl, lower alkoxycarbonyl or a lower alkyl group which may be substituted by hydroxy, lower alkoxy, phenoxy, diloweralkylamino, pyrrolidino, piperidino, or morpholino groups; $R^3$ further represents cycloalkyl of 5 to 7 carbon atoms or a phenyl group which may be substituted by chloro or a lower alkoxy radical; or $R^2$ and $R^3$ together with the nitrogen atom to which they are attached form an aziridine, pyrrolidine, piperidine, morpholine or piperazine ring which may be substituted by lower alkyl, hydroxyloweralkyl, phenylloweralkyl, phenyl or acetyl groups; or A and B together with the C=N group may form a 5, 6 or 7-membered N-heterocyclic ring.

In the group of the most preferred compounds according to formula I, Y and A are both hydrogen atoms, R' is a lower alkyl or alkoxy-alkyl group containing up to 5 carbon atoms, $R^2$ is hydrogen and $R^3$ is a dialkylaminoalkyl group containing up to 7 carbon atoms, an alkoxyalkyl group containing up to 6 carbon atoms or a pyrrolidinoethyl, piperidinoethyl, or morpholinoethyl group.

The reaction is carried out in the presence of either an alkali metal, alkali metal hydride, alkoxide, hydroxide, or carbonate, and a suitable solvent. Among the solvents that have been found to be suitable are water, lower alcohols, benzene, toluene, xylene, dioxane, tetrahydrofurane, and dimethylsulfoxide.

The reaction is further carried out at temperatures of 20°–150° C, preferably at 60°–80° C, with the reaction times being between 30 minutes and several hours in length.

Following this procedure, it is not necessary to use the imidates or amidines of formula III in substance; the solutions employed for the preparation of the specific imidates or amidines may be used directly.

The compounds prepared according to this procedure may be further transformed into physiologically acceptable salts following recognized pharmaceutical protocols.

According to a second procedure:

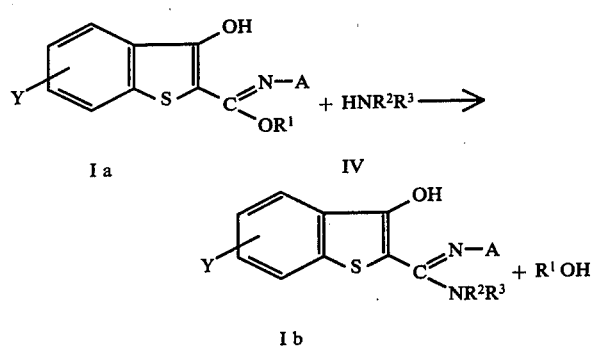

compounds of the general formula I b can also be obtained by reacting compounds of the general formula Ia with amines of the general formula IV without a solvent or in a suitable solvent such as water, a lower alcohol, dimethylformamide, or dimethylsulfoxide, or in an excess of amine of the formula IV at temperatures from 0° to 150° C, preferably at 20°–70° C. A, Y, $R^1$, $R^2$, and $R^3$ have the meanings given in the first procedure above.

The compounds prepared according to this procedure may be further transformed into physiologically acceptable salts following recognized pharmaceutical protocols.

According to a third procedure:

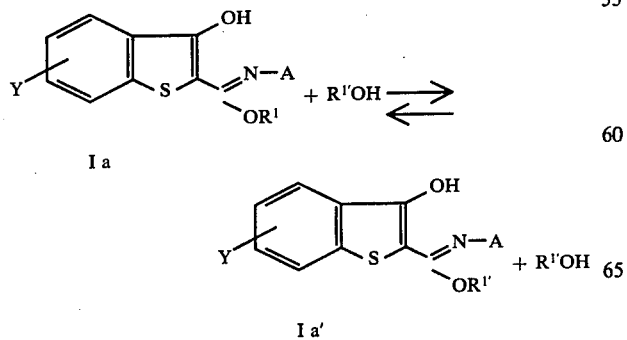

compounds of the formula Ia or Ia' may reciprocally be converted into each other by transesterification with alcohols of the formula $R^{1'}OH$ or $R^1OH$ with an exchange between $R^1$ and $R^{1'}$ taking place and $R^{1'}$ having the meaning stated for $R^1$. Y, A, and $R^1$ have the meanings given above.

The properties of the new compounds and their methods of preparation under the three procedures outlined above are demonstrated by the following examples which are to illustrate, but not limit the present invention.

EXAMPLE 1

Methyl 3-hydroxy-benzo[b]thiophene-2-carboximidate a. A solution of 0.46 g (0.02 mol) of sodium in 150 ml of methanol is mixed with 15.1 g (0.2 mol) of chloroacetonitrile and stirred at room temperature for 1 hour. This mixture is added dropwise to a solution of 33.6 g. (0.2 mol) of methyl thiosalicylate and 4.6 g. (0.2 mol) of sodium in 200 ml of methanol. The mixture thus obtained is heated under reflux for 30 minutes, poured into water, and the precipitate filtered off. Recrystallization from ethyl acetate/acetone solution yields 30.2 g of yellow crystals with an m.p. of 201° C.

b. A solution of 0.46 g (0.02 mol) of sodium in 150 ml of methanol is mixed with 15.1 g (0.2 mol) of chloroacetonitrile and stirred at room temperature for 1 hour. This mixture is added dropwise to a solution of 33.6 g (0.2 mol) of methyl thiosalicylate and 11.2 g (0.2 mol) of potassium hydroxide in 200 ml of water. The mixture thus obtained is heated under reflux for 2 hours, diluted with water, and the precipitate is recrystallized from ethyl acetate/acetone solution.

c. A solution of 23 g (1 mol) of sodium in 1 l of anhydrous methanol is mixed with 84 g (0.5 mol) of methyl thiosalicylate while stirring. This is then mixed with 79 g (0.5 mol) of ethyl chloro-acetimidate hydrochloride and heated under reflux for 10 hours. The sodium chloride precipitate is filtered off and the desired product isolated by evaporation (yield: 73 g, m.p. 201° C).

The compound obtained in either of the three protocols above is, based upon the melting point of 201° C, of the same purity.

EXAMPLE 2

Ethyl 3-hydroxy-benzo[b]thiophene-2-carboximidate a. This compound is prepared as described in Example 1(a) using ethanol instead of methanol. Yield is 30 g of yellow crystals with an m.p. of 194° C.

b. The reaction described in Example 1(c) is repeated using anhydrous ethanol instead of methanol to obtain the compound stated above.

c. 33.6 g of methyl thiosalicylate are dissolved in 400 ml of anhydrous dioxane. Adding 9.6 g of sodium hydride in a 50 percent oil suspension yield the sodium salt, precipitated as a yellow, voluminous precipitate. A solution of 24.3 g of ethyl chloroacetimidate in 200 ml of anhydrous dioxane is added dropwise to this suspension while stirring, and the mixture is heated to 70° for 2 hours. It is then poured into water and the product isolated by filtration.

The compound obtained in either of the three protocols above is, based upon the melting point of 194° C, of the same purity.

EXAMPLE 3

Propyl 3-hydroxy-benzo[b]thiophene-2-carboximidate 16.8 g (0.1 mol) of methyl thiosalicylate are added dropwise to a solution of 4.6 g (0.2 mol) of sodium in 400 ml of anhydrous n-propanol. To this mixture 17.2 (0.1 mol) of propyl chloroacetimidate hydrochloride are slowly added and the resultant mixture is heated under reflux for 6 hours. The reaction mixture is evaporated under vacuum and the residue distributed between water and dichloromethane. The organic phase is dried, evaporated, and the residue recrystallized from ethyl acetate/diisopropylether solution to yield 6.2 g of yellow crystals with an m.p. of 185° C.

EXAMPLE 4

Isopropyl 3-hydroxy-benzo[b]thiophene-2-carboximidate 20 g of methyl 3-hydroxy-benzo[b] thiophene-2-carboximidate (Example 1) are heated under reflux in 500 ml of isopropanol for three days. The methanol being formed is constantly distilled off by passing through a stream of nitrogen. Evaporation to dryness and recrystallization of the residue from ethyl acetate yields yellow crystals with an m.p. of 208° C.

EXAMPLE 5 n-Butyl 3-hydroxy-benzo[b]thiophene-2-carboximidate

A solution of 12 g of methyl 3-hydroxy-benzo[b]thiophene-2-carboximidate (Example 1) in 300 m. of anhydrous n-butanol is heated under reflux for 4 hours and then concentrated to yield upon crystallization from ethyl acetate solution yellow crystals having an m.p. of 185° C.

The compounds of the general formula I listed in table I can be prepared in the same manner as described in Examples 1–5. In the formula, A would represent hydrogen, and B would represent —O—$R_1$. $R_1$ would be derived from the corresponding alcohols as it was in Examples 1–5.

TABLE I

| Ex. | $R_1$ | m.p.(° C) | solvent |
|---|---|---|---|
| 6 | $C_6H_{11}$ | 198 | ethyl-methyl-ketone |
| 7 | CH(CH$_2$—CH$_3$)(CH$_3$) | 200 | ethyl acetate |
| 8 | CH$_2$—CH(CH$_3$)(CH$_3$) | 211–212 | ethyl acetate |
| 9 | CH$_2$—C(CH$_3$)$_3$ | 212–212 | ehtyl acetate |
| 10 | CH$_2$—CH$_2$—OCH$_3$ | 143–144 | ethyl acetate/petroleum ether |
| 11 | CH$_2$—CH$_2$—OC$_2$H$_5$ | 114–116 | ethyl acetate/petroleum ether |
| 12 | CH$_2$—CH$_2$—OC$_6$H$_5$ | 169–171 | ethyl acetate/petroleum ether |
| 13 | CH$_2$—C$_6$H$_5$ | 155–157 | ethanol |
| 14 | CH$_2$—CH$_2$—C$_6$H$_5$ | 160–161 | ethyl acetate |
| 15 | CH$_2$—CH$_2$—OH | 169 | acetone |
| 16 | CH$_2$—CH$_2$—CH$_2$—OH | 178 | acetone/dioxane |

EXAMPLE 17

2-amidino-3-hydroxy-benzo[b]thiophene a. To a solution of 8.7 g (0.38 mol) of sodium in 350 ml of methanol are added first 32.1 g (0.19 mol) of methyl thiosalicylate and then 25 g (0.19 mol) of 2-chloroacetamidine-hydrochloride. After heating under flux for 4 hours, and evaporation under vacuum, the residue is dissolved in dilute hydrochloric acid. After extraction with ether the aqueous phase is alkalized, and the residue filtered and recrystallized from an ethanol/water solvent solution. 32.9 g of yellow crystals are obtained with an m.p. of 249° C (decomp.).

b. 3 g of methyl 3-hydroxy-benzo[b]thiophene-2-carboximidate (Example 1) in 100 ml of concentrated aqueous ammonia solution and 10 ml of methanol are stirred at room temperature for 20 hours. The precipitate is filtered and recrystallized from ethyl acetate/isopropanol solvent solution yielding 2.5 g of yellow crystals.

c. 3 g of methyl 3-hydroxy-benzo[b]thiophene-2-carboximidate (Example 1) are dissolved in 100 ml of methanol and heated under reflux for 10 hours while bubbling a stream of ammonia through the mixture. The residue obtained after evaporation of the solvent is recrystallized from ethyl acetate/isopropanol solvent solution yielding 2.5 g of yellow crystals.

The compound obtained in ether of the protocols above is, based upon the melting point of 249° C, of the same purity.

EXAMPLE 18

2-(N-ethyl-amidino)-3-hydroxy-benzo[b]thiophene a. To a solution of 6.4 g (0.28 mol) of sodium in 400 ml of methanol first 23.6 g (0.14 mol) of methyl thiosalicylate, then 22 g (0.14 mol) of N-ethyl-2-chloroacetamidine-hydrochloride are added and the mixture is heated under reflux for 6 hours. Further processing is according to Example 17a. Yield upon recrystallization from an ethyl acetate/isopropanol solution is 13 g of yellow crystals having an m.p. of 196° C.

b. 3 g of ethyl 3-hydroxy-benzo[b]thiophene-2-carboximidate (Example 2) are heated under reflux for 10 hours in 20 g of 33% aqueous ethylamine solution. The residue obtained after evaporation is recrystallized from an ethyl acetate isopropanol solution and yields 2 g of the product.

The compounds obtained above are, based upon the melting point of 196° C, of the same purity.

EXAMPLE 19

2-(N-amino-amidino)-3-hydroxy-benzo[b]thiophene

A solution of 21 g of methyl 3-hydroxy-benzo[b]thiophene-3-carboximidate (Example 1) in 250 ml of methanol is mixed with 10 g of 100% hydrazine hydrate and heated under reflux for 1.5 hours. Subsequently the mixture is cooled in an ice bath, the precipitate filtered and recrystallized from diethyleneglycol monoethyl ether solution to yield 19.4 g of yellow crystals having an m.p. of 242° C (decomp.).

The compounds listed in Table II can be prepared in the same manner as described in Examples 17–19. (In formula I, A would represent hydrogen).

TABLE II

| Ex. | B | m.p.(° C) | solvent |
|---|---|---|---|
| 20 | N(C$_2$H$_5$)$_2$ | 166 | ethanol/water |
| 21 | NH—C$_6$H$_{11}$ | 273 | methanol |
| 22 | NH—C$_4$H$_9$ | 223 | isopropanol |
| 23 | NH—CH$_2$—C$_6$H$_5$ | 228–9 | ethanol/water |
| 24 | NH—(CH$_2$)$_2$—C$_6$H$_5$ | 171–2 | ethyl accetate |

TABLE II-continued

| Ex. | B | m.p.(° C) | solvent |
|---|---|---|---|
| 25 | N(CH₂)(CH₂) (aziridine ring) | 198 | methanol |
| 26 | pyrrolidin-1-yl | 265-7 | dimethylformamide |
| 27 | piperidin-1-yl | 173 | ethyl acetate/ isopropanol |
| 28 | morpholin-4-yl (N–O ring) | 171 | isopropanol |
| 29 | NH(CH₂)₃—N(CH₃)₂ | 234 | ethanol |
| 30 | NH(CH₂)₂—N(C₂H₅)₂ | 133 | ethyl acetate/ petroleum ether |
| 31 | NH—(CH₂)₂—N(CH₃)₂ | 172,5 | ethyl acetate/ isopropanol |
| 32 | NH—(CH₂)₂—N(piperidinyl) | 265 | ethanol |
| 33 | NH—(CH₂)₂—N(morpholinyl) | 270 | ethanol |
| 34 | NH—(CH₂)₂—N(pyrrolidinyl) | 253-5 | ethanol |
| 35 | NH—(CH₂)₃—N(morpholinyl) | 280 | ethanol |
| 36 | NH—(CH₂)₃—N(C₂H₅)₂ | 115-6 | ethyl acetate |
| 37 | NH—(CH₂)₂—OH | 242 | dimethylformamide/ water |
| 38 | NH—(CH₂)₂—OCH₃ | 194 | isopropanol |
| 39 | NH—(CH₂)₂—OC₂H₅ | 150 | ethyl acetate |
| 40 | NH—(CH₂)₃—OCH₃ | 165 | isopropanol |
| 41 | NH—(CH₂)₃—OC₂H₅ | 127 | ethyl acetate |
| 42 | NH—(CH₂)₃—O—CH(CH₃)₂ | 129 | ethyl acetate |
| 43 | NH—(CH₂)₃—OCH₉ | 133 | ethyl acetate |
| 44 | NH(CH₂)₃—O—Cl₂—CH(CH₃)₂ | 137 | ethyl acetate |
| 45 | NH—(CH₂)₂—OC₆H₅ | 146-7 | isopropanol |
| 46 | N(CH₂—CH₂—OC₆H₅)₂ | 145-7 | methanol |
| 47 | NH—C₆H₄—OCH₃ (p) | 224-5 | ethanol/ acetone |
| 48 | piperazine N—NH · H₂O | 119 | water |
| 49 | piperazine N—N—CH₃ | 273 | ethanol |
| 50 | piperazine N—N—CH₂—C₆H₅ | 267 | ethanol |
| 51 | piperazine N—N—C₆H₅ | 183-4 | isopropanol |
| 52 | piperazine N—N—(CH₂)₂—OH | 165-6 | isopropanol |
| 53 | piperazine N—N—CO—CH₃ | 150-1 | ethyl acetate/ tetrahydrofurane |
| 54 | NH—OH | 192 | methanol |
| 55 | NH—NH—C₆H₅ | 220 | acetonitril/ dimethylformamide |
| 56 | NH—N(CH₃)₂ | 249 | acetone/isopropanol |
| 57 | NH—N(piperidinyl) | 253 | acetone |
| 58 | NH—N=C(CH₃)₂ | 240 | methanol |
| 59 | NH—N=C(COOH)(CH₃) | 316 | methanol |
| 60 | NH—NH—CO—(3-pyridyl) | 299-301 | dimethylformamide/ water |
| 61 | NH—NH—CO—(4-pyridyl) | 318-320 | ethanol |
| 62 | NH—NH—COH | 227-8 | methanol |
| 63 | NH—NH—CO—CH₃ | 220 | ethanol |
| 64 | NH—NH—CO—C₆H₅ | 304 | methanol |
| 65 | NH—NH—CO—CC₂H₅ | >330 | ethanol |
| 66 | N(C₂H₆)₃ | 185 | isopropanol |

EXAMPLE 67

2-(N,N'-diphenyl-amidino)-3-hydroxy-benzo[b]thiophene

A solution of 2.3 g (0.1 mol) of sodium in 150 ml of methanol is mixed with 16.8 g (0.1 mol) of methyl thiosalicylate and then a solution of 24.4 g (0.1 mol) of N,N'-diphenyl-2-chloroacetamidine in 250 ml of methanol is added. After heating under reflux for 1 hour, the mixture is poured into ice water and the precipitate filtered and recrystallized from an ethanol/water solution to yield 26.5 g of yellow needles having an m.p. of 152-153° C.

EXAMPLE 68

2-(N,N'-bis-p-ethoxyphenyl-amidino)-3-hydroxy-benzo[b]thiophene 5.2 of methyl thiosalicylate are reacted as in Example 67 with 1.4 g of sodium and 12.7 g of N,N'-bis(p-ethoxyphenyl)-2-chloro-acetamidine-nitrate in 300 ml of anhydrous ethanol. After recrystallization from methanol/water 12.3 g of yellow crystals are obtained which sinter to a glassy mass at a temperature of 87°–90° C and melt at 118°–122° C.

EXAMPLE 69

2-(N-phenyl-N'-diethyl-amidino)-3-hydroxy-benzo[b]-thiophenehydrochloride 16.8 g of methyl thiosalicylate are reacted as in Example 67 with 6.9 g of sodium and 31.6 g of N,N-diethyl-N'-phenyl-2-chloro-acetamidine-oxalate in 700 ml of anhydrous methanol. After reaction is completed, the product is evaporated under reduced pressure and the residue distributed between water and dichloromethane. The organic phase is dried and evaporated, and the oily residue dissolved in ethyl acetate and transformed into the hydrochloride by the introduction of hydrogen chloride. Yield upon purification from an ethanol/isopropanol solution is 10 g having an m.p. of 232° C.

EXAMPLE 70

Phenyl 3-hydroxy-benzo[b]thiophene-2-N-phenyl-carboximidate

Following the protocol of Example 67, 9 g of yellow needles are obtained from reacting 21.8 g of methyl thiosalicylate, 6 g of sodium, and 32.1 g of phenyl N-phenyl-chloroacetimidate in 300 ml of methanol. These have an m.p. of 146°–147° C and are recrystallized from an ethyl acetate/diisopropylether solution.

EXAMPLE 71 p-methoxy-phenyl 3-hydroxy-benzo[b]thiophene-2-N-phenyl-carboximidate

A solution of 16.8 g (0.1 mol) of methyl thiosalicylate in 100 ml of anydrous dioxane is added dropwise to a suspension of 4.8 g (0.1 mol) of sodium hydride (50% oil suspension) in 300 ml of anhydrous dioxane while stirring. The sodium salt of the methyl thiosalicylate separates as a yellow, voluminous precipitate. To this suspension is added dropwise a solution of 27.5 g (0.1 mol) of p-methoxy-phenyl N-phenyl-chloroacetimidate in 80 ml of anhydrous dioxane, the mixture is then heated to 70° C for 1 hour and evaporated under reduced pressure. The residue is mixed with water and extracted with dichloromethane. After evaporation of the dried organic phase a residue remains which is recrystallized from ethyl acetate/diisopropylether solution. Analysis of the product shows: Yield: 8.1 g of yellow crystals, m.p. 145° C.

EXAMPLE 72 p-chloro-phenyl-N-phenyl 3-hydroxy-benzo[b]thiophene-2-N-phenyl-carboximidate

Preparation follows the protocol of Example 71 using 28 g of p-chloro-phenyl N-phenyl-chloroacetimidate instead of p-methoxy-phenyl N-phenyl-chloroactimidate. Analysis of the product when crystallized from an ethyl acetate/diisopropyl ether shows: Yield: 5.4 g of yellow crystals with an m.p. of 138° C.

EXAMPLE 73

Ethyl 3-hydroxy-benzo[b]thiophene-2-N-phenyl-carboximidate

Following the protocol of Example 67, 17 g of ethyl N-phenyl-chloroacetimidate and 15 g of methyl thiosalicylate are reacted with 4 g of sodium in anhydrous ethanol. Crystallization from ethanol yields 17 g of yellow crystals with an m.p. of 80°–81° C.

EXAMPLE 74

Ethyl 5-chloro-3-hydroxy-benzo[b]thiophene-2-carboximidate

This compound is prepared as described in Example 2a using methyl 5-chloro-thiosalicylate instead of methyl thiosalicylate. Crystallization from acetone/ethanol solution yields yellow crsytals with an m.p. of 236° C.

EXAMPLE 75

Ethyl 6-chloro-3-hydroxy-benzo[b]thiophene-2-carboximidate

Reacting methyl 4-chloro-thiosalicylate according to the procedures of Example 2a yields the desired compound. Recrystallization from acetone/ethanol solution yields a product in the form of yellow crystals with an m.p. of 226° C.

EXAMPLE 76

2-(2'-imidazolin-2'-yl)-3-hydroxy-benzo[b]thiophene a. To a solution of 2.3 g (0.1 mol) of sodium in 250 ml of anhydrous methanol are added 15.4 g (0.1 mol) of thiosalicylic acid, 15.5 g (0.1 mol) of 2-chloromethylimidazoline-chydrochloride, and the mixture is heated under reflux for 6 hours. After evaporation under reduced pressure, dissolution of the residue in methanol water solution, and mixing with ammonia, the yellow precipitate (6 g) is filtered off and recrystallized from n-propanol/dimethylformamide soltuion to yield the product having an m.p. of 304° C (decomp.)

1. 11.2 g of 2-(2-imidazolinyl-methyl-thio)-benzoic acid hydrochloride, m.p. 175° (crystallized from isopropanol solution) are obtained by evaporating the aqueous - alkaline filtrate, mixing the residue with concentrated hydrochloric acid, and filtering the colorless precipitate. Heating above the melting point causes cyclisation to the title compound with the splitting off of a water and hydrogen chloride molecules.

b. A solution of 15.5 g (0.075 mol) of methyl 3-hydroxybenzo[b]thiophene-2-carboximidate (Example 1) is slowly dropped into a boiling solution of 18 g (0.3 mol) of ethylene-diamine in 10 ml of methanol. The mixture is kept boiling for 2 hours, then cooled in an ice bath and the precipitate filtered. Recrystallization from dimethylformamide/water solution yields 7.4 g of yellow crystals with an m.p. of 304° C.

The compounds listed in Table III can be produced in a similar manner to Example 76.

TABLE III

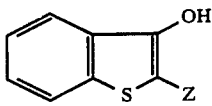

| Ex. | Z | m.p.° C | solvent |
|---|---|---|---|
| 77 | -C(=N-CH₂-CH₂)(NH-CH₂) (6-membered ring with N-CH₂-CH₂-NH) | 280 | ethanol/water |
| 78 | -C(=N-CH₂-CH₂)(NH-CH₂-CH₂) | 246 | ethyl acetate/isopropanol |
| 79 | -C(=N-N)(NH-CH₂) | 233 | ethyl acetate |
| 80 | -C(=N-CO)(NH-CH₂) | >300 | methanol |
| 81 | -C(=N-C(CH₃))(NH-N) | 301-3 | methanol |
| 82 | -C(=N-C-Pyridyl(-4))(NH-N) | >250 | dimethylformamide/water |
| 83 | -C(=N)(NH) fused benzene | 290 | methyl-ethyl-ketone/dimethylformamide |
| 84 | -C(=N)(O) fused benzene | 240-2 | acetone |
| 85 | -C(=N)(S) fused benzene | 194-6 | ethanol |
| 86 | -C(=N-CH₂)(O-CH₂) | 216-7 | acetone |

The Benzo[b]thiophenes and their pharmaceutically usable salts prepared according to the invention exhibit novel and valuable pharmacological properties. They especially exhibit anti-inflammatory effects with a resultant low toxicity and with the absence of the typical ulcerating effect on the mucous membranes of the digestive tract as found resulting from many commercially available anti-inflammatory ingredients.

To show the utility and safety of the compounds of the invention when used for their anti-inflammatory properties, the following series of tests were performed.

PHARMACOLOGICAL RESULTS

The compound, ethyl-3-hydroxy-benzo(b)thiophene-2-carboximidate (Example 2) is chosen as a typical representative of the group of benzo[b] thiophene, although results on other compounds of this invention also appear. This substance has pharmacological properties similar to those known as active anti-inflammatory preparations with analgesic and antipyretic properties, such as phenylbutazone (4-n-Butyl-1,2-diphenyl-3,5-dioxo-pyrazolidine), azapropazone (3-Dimethylamino-7-methyl-1,2-(n-propylmalonyl)-1,2-dihydro-1,2-benzotriazine-dihydrate),acetylsalicylic acid (Aspirin), and indomethacin (1-(p-Chlorobenzoyl)-5-methoxy-2-methylindole-3-acetic acid).

In order to show the superiority of these novel compounds over that of the known anti-inflammatory preparation, the following pharmacological tests were carried out on both the novel compounds and the four known preparations above. A comparison of the results obtained shows the superiority of the compounds according to this invention.

A. ACUTE TOXICITY:

Experimental animals are male mice (NMRI) weighing 16 to 24 g and male rats (SIV 50) weighing 120 to 180 g.

Prior to the beginning of the test, all animals are kept fasting for 16 to 18 hours, however water is offered ad libitum. 6 mice and 4 or 6 rats belonged to each dosage group and the doses between each group are increased logarithmically. The volume of liquid administered during testing amounted to 2 ml/100 g body weight. The substances tested are suspended in 1 percent Tragacanth mucilage and administered intragastrically via a gastric tube.

The results based upon the LD50 for the compounds tested are tabulated below.

| | Acute Toxicity in Mice and Rats | | | Confidence Limits in mg/kg R=0.09 | |
|---|---|---|---|---|---|
| Animal | Substance | Route of Administration | LD$_{50}$ mg/kg | lower | upper |
| Mouse | Example 2 | i.g. | 3.890 | 3.268 | 4.629 |
| Mouse | indomethacin | i.g. | <10 | — | — |
| Mouse | Azapropazone | i.g. | ca.3.000 −5.000 | — | — |
| Mouse | Phenylbutazone | i.g. | 714 | 517.3 | 985.3 |
| Mouse | Acetylsalicylic Acid | i.g. | 1.878 | 1.433 | 2.460 |
| Rat | Example 2 | i.g. | 4.000 | — | — |
| Rat | Indomethacin | i.g. | 20-30 | — | — |
| Rat | Azapropazone | i.g. | ca.3.000 −6.000 | — | — |
| Rat | Phenylbutazone | i.g. | 598 | 524.5 | 681.7 |
| Rat | Acetylsalicylic Acid | i.g. | 2.065 | 1.298 | 3.289 |

B. YEAST EDEMA AND DETERMINATION OF PAIN THRESHOLD:

Test animals are male rats (SIV 50) weighing 100 to 180 g. All animals are kept fasting for 16 to 18 hours prior to the beginning of the test, however, water is offered ad libitum. 10 animals belonged to each dosage group. The volume of liquid administered during testing amounted to 2 ml/100 g body weight. The substances tested are suspended in 1 percent Tragacanth mucilage and administered intragastrically via a gastric tube.

The volume of the paw is determined according to the method described by Enders and Heidbrink, the pain threshold according to that described by Randall and Selitto (Arch. Int. Pharmacodyn CXI: 409, 1957).

Following initial measurements, 0.05 mole of a 5% suspension of dried yeast is injected subplantarly into the right paw and the test substances are administered immediately. The blank control group is given Tragacanth mucilage only. After 3 hours the pain threshold and the volume of the paw are determined again.

The mean value of the increase in paw volume of the animals of the blank control after 3 hours is rated 100%, and the mean value of the increase in paw volume of the animals of the substance groups expressed as a percentage thereof. Pain threshold after 3 hours reflects the increase or decrease in percent, compared to the initial value.

In order to be able to calculate the $ED_{50}$ according to the method by Lichtfield and Wilcoxon (J.P.E.T. 96:99, 1949), those animals in a dose group are considered protected when the paw swelling was at least 40% less than that of the blank control.

The results based upon both increase in paw volume and pain threshold for the materials tested are tabulated below.

Influence of the Example 2 compound, Indomethacin, Phenylbutazone, Azapropazone, and Acetylsalicylic Acid on the Yeast Edema of the Rat Paw

| Substance | Dose mg/kg | Volume % | Pain Threshold | Number of Animals |
|---|---|---|---|---|
| Tragacanth | — | 100 | − 17 | 100 |
| Example 2 | 31.2 | 77 | + 10 | 10 |
| Example 2 | 62.5 | 50 | + 46 | 10 |
| Example 2 | 125.0 | 35 | + 5 | 10 |
| Indomethacin | 5.0 | 131 | − 22 | 10 |
| Indomethacin | 20.0 | 108 | + 11 | 10 |
| Phenylbutazone | 150.0 | 74 | − 9 | 10 |
| Phenylbutazone | 300.0 | 67 | + 3 | 10 |
| Azapropazone | 250.0 | 98 | + 6 | 10 |
| Azapropazone | 400.0 | 100 | − 52 | 10 |
| Acetylsalicylic Acid | 150.0 | 134 | − 6 | 10 |
| Acetylsalicylic Acid | 300.0 | 81 | − 15 | 10 |

C. CARRAGEENIN EDEMA

Test animals used are the same as stated under Example B and up to the initial measurement, the procedure corresponded to that described under this example.

After an initial measurement, the test substances are administered and after 60 minutes a 1% Carrageenin suspension is injected subplantarly (0.1 ml/paw). After 60 and 180 minutes the paw volume is again determined. Here, too, the blank control group was treated with the carrier alone.

The increase in the volume of the paw after 60 minutes is considered as the first phase of the biphase edema and that after 180 minutes, as compared to the 60-minute-value, as the second phase. Moreover, the total increase of the paw edema within 180 minutes, as compared to the initial value, is also determined.

Determination of the influence exerted by the substances upon the development of the paw edema and calculation of the $ED_{50}$ are done as under Example B.

The results showing the effects of the materials tested upon the biphase edema are tabulated below:

Influence of the Example 2 compound, Indomethacin, Phenylbutazone, Azapropazone, and Acetylsalicylic Acid on the Carrageenin Edema of the Rat Paw

| Substance | Dose mg/kg | 1st Phase % | 2nd Phase % | 3 Hrs. % |
|---|---|---|---|---|
| Example 2 | 62.5 | 65 | 73 | 62 |
| Example 2 | 125.0 | 65 | 27 | 42 |
| Example 2 | 250.0 | 29 | 20 | 25 |
| Indomethacin | 1.0 | 65 | 80 | 73 |
| Indomethacin | 5.0 | 80 | 73 | 73 |
| Phenylbutazone | 60.0 | 114 | 52 | 77 |
| Phenylbutazone | 50.0 | 81 | 15 | 38 |
| Azapropazone | 100.0 | 72 | 50 | 63 |
| Azapropazone | 400.0 | 79 | 21 | 55 |
| Acetylsalicylic Acid | 100.0 | 83 | 114 | 96 |
| Acetylsalicylic Acid | 200.0 | 95 | 60 | 76 |

D. KAOLIN EDEMA

Test animals used are the same as stated under Example B and up to the beginning of the test, the procedure corresponded to that described under this example.

After an initial measurement, a sterile 25% kaolin suspension was injected (0.05 ml/paw) subplantarly. The test substances are administered immediately, and after 60, 120, and 180 minutes the paw volume is again determined.

Evaluation of the tests was performed as stated under Example C, and the results so obtained presented below:

Influence of the Example 2 compound, Indomethacin, Phenylbutazone, Azapropazone, and Acetylsalicylic Acid on the Kaolin Edema of the Rat Paw

| Substance | Dose mg/kg | 60 Minutes % | 120 Minutes % | 180 Minutes % |
|---|---|---|---|---|
| Tragacanth | — | 100 | 100 | 100 |
| Example 2 | 25.0 | 36 | 44 | 50 |
| Example 2 | 50.0 | 62 | 40 | 5 |
| Indomethacin | 2.5 | 79 | 81 | 81 |
| Phenylbutazone | 90.0 | 107 | 100 | 81 |
| Azapropazone | 250.0 | 100 | 93 | 67 |
| Acetylsalicylic Acid | 300.0 | 156 | 93 | 82 |

E. COTTON-PELLET TEST

Test animals are male rats (SIV 50) weighing 110 to 200 g. All test animals are kept fasting for 16 to 18 hours prior to the implantation of the pellets; after that food and water were available ad libitum. Each dose level of the chemical tested was administered to 12 animals. The substances were suspended in 1% Tragacanth mucilage and administered intragastrically by means of a stomach tube. The substances to be investigated and the control suspensions are administered once on the operating day following operation, and twice a day on the following 6 days (at intervals of 6 to 8 hours). The type of application and volume of liquid corresponded to that under B.

Under light ether anesthesia 4 sterile cotton pellets were implanted under the skin on the back of the animal. The weight of one pellet was 50 mg ± 0.5 mg. After 7 days treatment, the animals werre sacrificed, the pellets removed with the granulation tissue, weighed and then dried in the incubator at +80° C to constant weight. The average dry weight of the granulation tissue of the control group was rated 100%, and deviations of the mean weights of the group treated with the test substance determined as a percentage thereof.

The weight of the animals is measured daily throughout the tests, and the percental increase determined. At the end of some tests, moreover, the suprarenal glands are removed and their weight determined.

The results obtained showing the deviation of the granulation tissue dry weight and changes in body weight are tabulated below.

The results based upon the materials tested are presented below.

Influence of the Example 2 compound, Indomethacin, Phenylbutazone, and Acetylsalicylic Acid on the Granuloma Pouch Weight and the Fluid of the Pouch

| Substance | Dose mg/kg | Granuloma Pouch Dry Weight % | Secretion % | Increase in Body Weight |
|---|---|---|---|---|
| Tragacanth | — | 100 | 100 | normal |
| Example 2 | 2 × 125 | 70 | 59 | not influenced |
| Indomethacin | 2 × 1.5 | 98 | 134 | not influenced+ |
| Phenylbutazone | 2 × 90 | 84 | 96 | not influenced |
| Acetylsalicylic Acid | 2 × 150 | 88 | 121 | not influenced |

+Exitus of an animal

Influence of the Example 2 compound, Indomethacin, Phenylbutazone, Azapropazone, and Acetylsalicylic Acid on Development of the Granulation Tissue in the Cotton-Pellet Test

| Substance | Dose mg/kg | Granulation Tissue % (Dry Weight) | Increase in Body Weight |
|---|---|---|---|
| Tragacanth | — | 100 | normal |
| Example 2 | 2 × 75 | 78 | not influenced |
| Indomethacin | 2 × 1.5 | 80 | not influenced |
| Phenylbutazone | 2 × 90 | 78 | not influenced |
| Azapropazone | 2 × 150 | 76 | not influenced |
| Acetylsalicylic Acid | 2 × 200 | 89 | not influenced |

F. GRANULOMA POUCH TEST

Test animals and the method of application of the dosages of the various test substances used are the same as under Example E.

Under light ether anesthesia 25 ml of air are injected under the shaved skin of the back. 0.5 ml of croton oil/animal (0.05%) are injected into the pouch formed by the air, and evenly distributed over the back by turning the animal.

On the third day croton oil (3%, 0.5 ml/animal) is again injected into this pouch. After being treated for 7 days the animals are sacrificed, the quantity of secretion in the granuloma pouch determined, the granuloma pouch removed, and the weight of the dry tissue is determined according to the process described under Example E.

The average dry weights of the granuloma pouches and the quantities of secretion of the groups subjected to treatment are then compared with those of the control group and the percental deviations calculated.

At the end of some tests the suprarenal glands are removed and the weight of these organs is also determined.

The weight of the animals is measured daily and the changes determined as a percentage.

G. ADJUVANT ARTHRITIS

Test animals used are the same as described under Example E; food and water is given ad libitum.

On the first day of the test a 0.8% suspension of *Mycobacterium butyrium* in paraffin (0.05 or 0.1 ml/paw) is injected subplanatarly into the left hind paw of the animals. After 18 days those animals in which the untreated hind paw showed no clear arthritis are withdrawn fron the test. From the 19th to the 22nd day the animals showing a reaction are treated intragastrically with the test substances. The right paw having been marked above the ankle-joint, the volume is determined daily from the 19th to the 22nd or 23rd day, according to the process described under Example B.

The volume of liquid, as well as of the carrier administered, corresponded to that described in the above tests.

The results based upon swelling of the animal's paw is tabulated below.

Influence of the Example 2 compound, Indomethacin, Phenylbutazone, and Azapropazone on Arthritis Induced by the Freund Adjuvant

| Substance | Dose mg/kg | Swelling % |
|---|---|---|
| Tragacanth | — | 100 |
| Example 2 | 2 × 125.0 | 81 |
| Indomethacin | 2 × 2.5 | 80 |
| Phenylbutazone | 2 × 60.0 | 84 |
| Azapropazone | 2 × 250.0 | 91 |

H. HOT-PLATE TEST:

Male mice (NMRI) weighing 18 to 28 g are used as test animals. The animals are placed on a copper plate constantly kept at 55° C, and the time is measured until they lick their forepaws.

Following 3 initial measurements, the test substances are administered intragastrically. Afterwards the measurements are repeated over a period of 2 hours at intervals of 30 minutes. Each dose is administered to 10 animals selected from groups of 15 animals following the initial measurements.

The test substances are administered as a suspension in 1% Tragacanth mucilage, the volume of liquid amounting to 2 ml/100 g of body weight.

For the purpose of statistical evaluation according to Litchfield and Wilcoxon, those animals in which the reaction time has been extended by at least 100% are considered protected.

The results are tabulated below.

Analgesic Activity of the Example 2 compound, Indomethacin, Phenylbutazone, Azapropazone and Acetylsalicylic Acid in Mice during the Hot-Plate Test

| Substance | $ED_{50}$ mg/kg | Confidence Limits in mg/kg $p = 0.05$ lower | upper | Notes |
|---|---|---|---|---|
| Example 2 | 87.8 | 33.5 | 14.39 | — |
| Indomethacin | — | — | — | slightly effective, starting with 20 mg/kg approx. 50% protection is achieved |
| Phenylbutazone | — | — | — | effect, but not dose dependent |
| Azopropazone | — | — | — | ineffective |
| Acetylsalicylic Acid | — | — | — | up to 400 mg/kg ineffective |

I. ANTIPYRESIS:

Test animals are male rats (SIV 50) weighing 100 to 180 g. 16 hours prior to the beginning of the test a 12% suspension of dried yeast (1 or 2 ml/100 g of body weight) is injected subcutaneously. When the maximum of the increase in body temperature is reached, following 3 to 4 initial measurements, the test substances are applied intragastrically and the development of the body temperature is observed for a period of 7 hours.

The test substances administered are suspended in Tragacanth mucilage; the volume of liquid administered amounting to 2 ml/100 g of body weight. In this test 2 control groups are used, one given sodium chloride subcutaneously (normal temperature group) and to the other group a yeast suspension is administered subcutaneously but, instead of the test substances, Tragacanth mucilage is administered intragastrically (fever control group).

The influence of the Example 2 compound and of the control substances on the increased body temperature of the rat are shown in the following graphs, which clearly show the superiority of the Example 2 substance for decreasing body temperature.

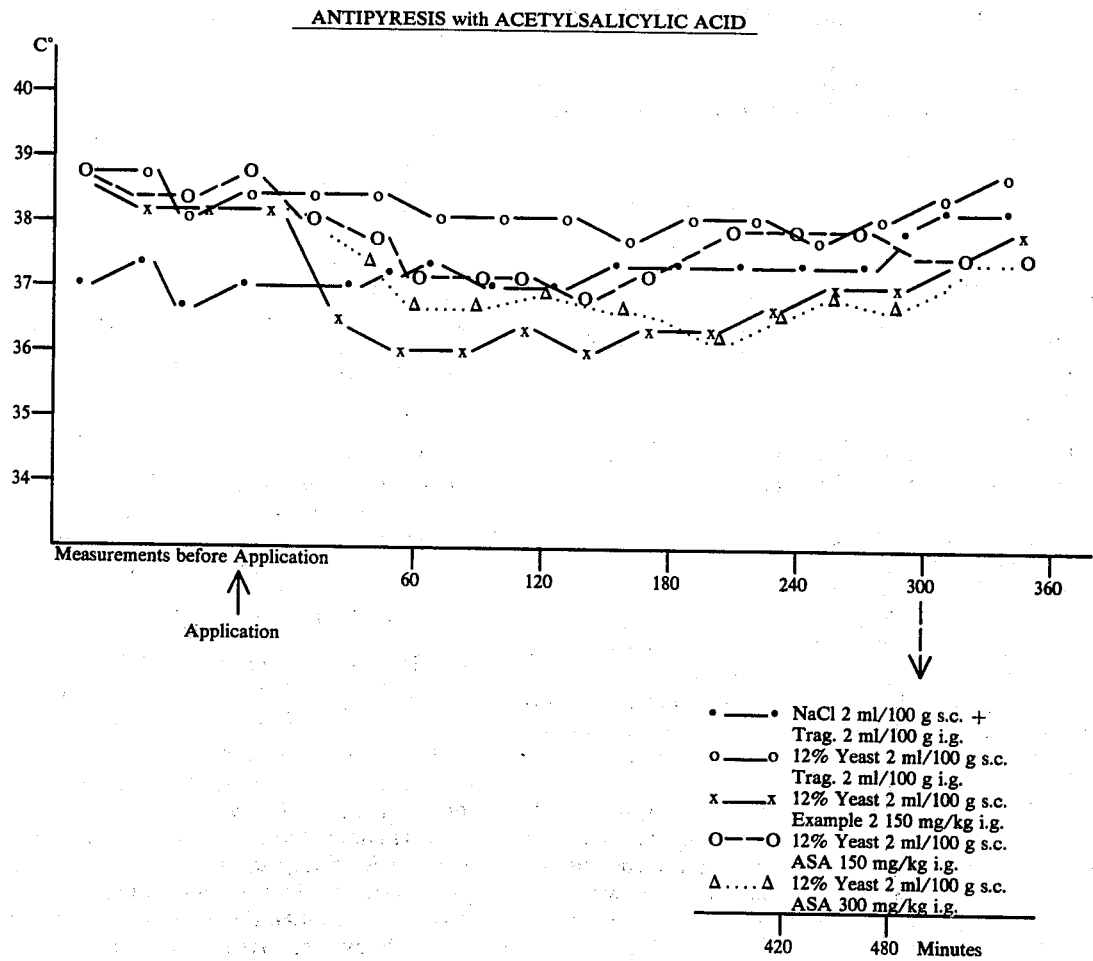

ANTIPYRESIS with ACETYLSALICYLIC ACID

• —— • NaCl 2 ml/100 g s.c. + Trag. 2 ml/100 g i.g.
o —— o 12% Yeast 2 ml/100 g s.c. Trag. 2 ml/100 g i.g.
x —— x 12% Yeast 2 ml/100 g s.c. Example 2 150 mg/kg i.g.
O — — O 12% Yeast 2 ml/100 g s.c. ASA 150 mg/kg i.g.
△ .... △ 12% Yeast 2 ml/100 g s.c. ASA 300 mg/kg i.g.

ANTIPYRESIS with AZAPROPAZONE

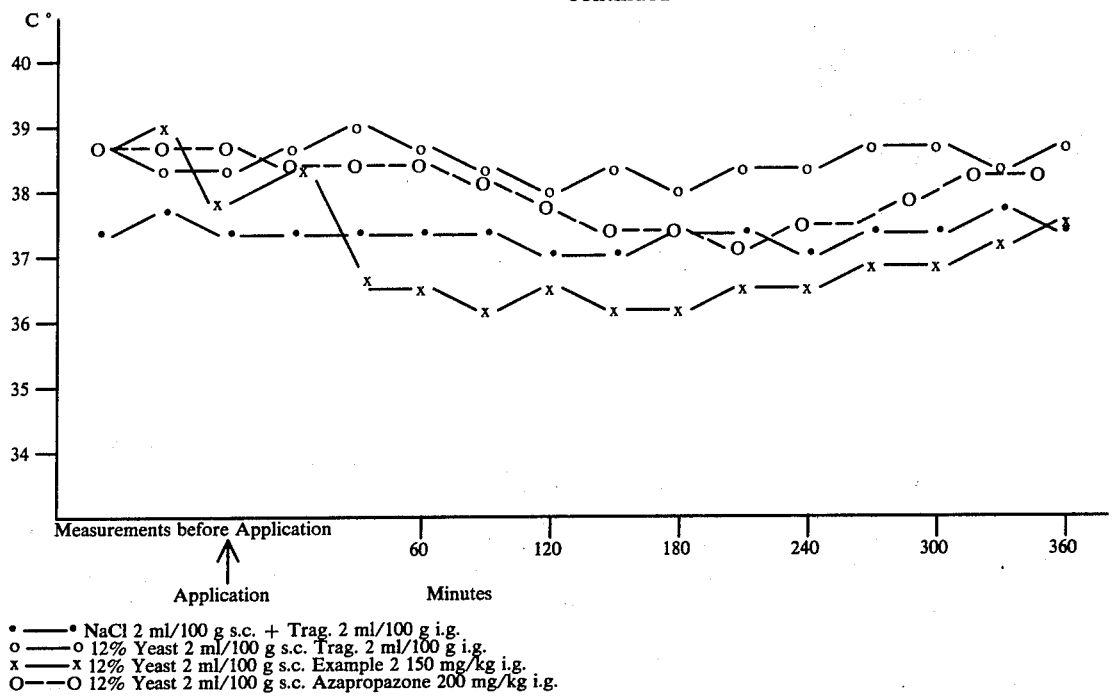

* •——• NaCl 2 ml/100 g s.c. + Trag. 2 ml/100 g i.g.
* o——o 12% Yeast 2 ml/100 g s.c. Trag. 2 ml/100 g i.g.
* x——x 12% Yeast 2 ml/100 g s.c. Example 2 150 mg/kg i.g.
* O——O 12% Yeast 2 ml/100 g s.c. Azapropazone 200 mg/kg i.g.

J. SUMMARY OF PHARMACOLOGICAL RESULTS FOR ETHYL-3-HYDROXY-BENZO (b) THIOPHENE-2-CARBOXIMIDATE (EXAMPLE 2):

Calculating the $ED_{50}$ on the basis of the results obtained from Examples A, B, and D, the following values are obtained.

| Substance | $ED_{50}$ mg/kg | Confidence Limits in mg/kg $p = 0.05$ | |
|---|---|---|---|
| | | lower | upper |
| Example 2 | 93.1 | 65.1 | 133.1 |
| Indomethacin | 0.9 | 0.31 | 2.54 |
| Phenylbutazone | 20.1 | 13.0 | 30.9 |
| Azapropazone | 117.0 | 73.5 | 186.0 |
| Acetylsalicylic Acid | 192.0 | 153.6 | 240.0 |

From the $ED_{50}$ and $LD_{50}$ (A) the following therapeutic ratios for this test are calculated:
Example 2; 42.9
Indomethacin; 33.3
Phenylbutazone; 29.7
Azapropazone;
Acetylsalicylic Acid; 10.7

According to this calculation, the therapeutic ratio for Ethyl-3-hydroxy-benzo(b)thiophene-2-carboximidate is very good. It is not possible to calculate a therapeutic ratio for Azapropazone, since, because of the evidently irregular absorption of the substance, no exact $LD_{50}$ is obtained.

As shown in (H), only the Ethyl-3-hydroxy-benzo(b)-thiophene-2-carboximidate showed sufficient analgesic activity in this experimental setup. In the case of the standard substances, the analgesic activities were not pronounced enough or there were no such activities so that it was not possible to calculate an $ED_{50}$.

While commercially available anti-inflammatory preparations exhibit an effect in some test models and are even ineffective in others, the anti-inflammatory effect of the Example 2 compound is proved in all test models. The strength of the effects achieved is of the same order as that of the most potent commercially available anti-inflammatory preparations. Compared to customary anti-inflammatory preparations, the analgesic activity of the Example 2 compound is particularly marked. The antipyretic effect is also seen to be stronger than that of comparable substances.

Doses as low as 50 mg/kg have a clear anti-inflammatory effect. In the hot plate test, 87.8 mg/kg extends the reaction time of 50 percent of the animals by 100%. In the antipyresis test, 150 mg/kg was considerably more effective than 300 mg/kg of acetylsalicylic acid.

Compared with toxicity levels of the standard substances used in the testing, those of the Examples 2 compound are very favorable. Owing to the low doses required for achieving anti-inflammatory, analgesic, and antipyretic effects, in extraordinarily favorable therapeutic ratio is also obtained.

K. PHARMACOLOGICAL RESULTS OF MORE BENZO(b)THIOPHENE DERIVATIVES ACCORDING TO THE INVENTION:

The methods applied for investigating these substances corresponded to those described under the above examples. In the hot plate test, however, the $ED_{50}$ was not determined, but prolongation of the reaction time following administration of the substance was shown directly. In the temperature test no graph was made of the results; the table showing the decrease of normal body temperature following administration of the substance.

The results obtained from the various pharmacological tests are tabulated below:

| Acute Toxicity in Mice | | |
|---|---|---|
| Substance | Route of administration | ED$_{50}$ mg/kg |
| Example 1 | ig. | > 1.600 |
| Example 30 | ig. | approx. 1.000 |
| Example 30 | ic. | approx. 1.000 |
| Example 31 | ig. | > 1.600 |
| Example 31 | sc. | > 800 |
| Example 31 | sc. | approx. 1.000 |
| Example 34 | sc. | approx. 600 |
| Example 10 | ig. | approx. 1.600 |
| Example 11 | ig. | > 1.600 |
| Example 41 | ig. | approx. 1.600 |

| Yeast Edema And Determination Of Pain Threshold In The Rat Paw | | | | |
|---|---|---|---|---|
| Substance | Route of administration | dose mg/kg | Volume % | pain threshold % |
| tragacanth | ig. | — | 100 | − 23 |
| Example 1 | ig. | 75 | 32 | − 10 |
| NaCl | sc. | — | 109 | − 20 |
| Example 30 | sc. | 150 | 53 | + 18 |
| tragacanth | ig. | — | 100 | − 39 |
| Example 31 | ig. | 200 | 75 | − 7 |
| NaCl | sc. | — | 100 | − 10 |
| Example 33 | sc. | 225 | 46 | + 34 |
| NaCl | sc. | — | 100 | − 10 |
| Example 34 | sc. | 125 | 54 | − 7 |
| tragacanth | ig. | — | 100 | − 9 |
| Example 41 | ig. | 125 | 51 | + 22 |
| tragacanth | ig. | — | 100 | − 32 |
| Example 10 | ig. | 200 | 73 | − 49 |
| tragacanth | ig. | — | 100 | − 35 |
| Example 10 | ig. | 250 | 33 | − 30 |
| tragacanth | ig. | — | 100 | − 15 |
| Example 11 | ig. | 200 | 41 | + 32 |
| indomethacin | ig. | 5 | 100 | − 22 |

| Influence On Carrageenin Edema Of The Rat Paw | | | | | |
|---|---|---|---|---|---|
| Substance | Route of administration | dose mg/kg | 1st phase % | 2nd phase % | 3 hrs. % |
| tragacanth | ig. | — | — | — | 100 |
| NaCl | se. | — | 100 | 100 | 100 |
| Example 1 | ig. | 75 | — | — | 43 |
| Example 30 | se. | 150 | 39 | 68 | 51 |
| Example 31 | se. | 150 | 58 | 32 | 37 |
| Example 33 | se. | 150 | 59 | 17 | 39 |
| Example 34 | se. | 100 | 47 | 44 | 44 |
| Example 10 | ig. | 250 | 79 | 36 | 53 |
| Example 11 | ig. | 250 | 62 | 43 | 54 |
| Example 41 | ig. | 125 | 78 | 28 | 51 |
| azapropazone | ig. | 400 | 79 | 21 | 55 |

| Influence On Kaolin Edema Of The Rat Paw | | | | | |
|---|---|---|---|---|---|
| Substance | Route of administration | dose mg/kg | 60 min. % | 120 min. % | 180 min. % |
| tragacanth | ig. | — | 100 | 100 | 100 |
| Example 10 | ig. | 200 | 67 | 47 | 46 |
| Example 11 | ig. | 50 | 40 | 36 | 56 |
| Example 11 | ig. | 100 | 22 | 27 | 46 |
| acetylsalicylic acid | ig. | 300 | 156 | 93 | 82 |

| Influence On The Development Of Granulation Tissue In The Cotton Pellet Test | | | | |
|---|---|---|---|---|
| Substance | Route of administration | dose mg/kg daily | granulation tissue % dry weight | increase in body weight % |
| NaCl | sc. | — | 100 | 27 |
| indometacin | ig. | 2×1,5 | 91 | 17 |
| Example 30 | sc. | 2×50,0 | 82 | 27 |
| Example 30 | sc. | 2×75,0 | 68 | 27 |
| tragacanth | ig. | — | 100 | 36 |
| indomethacin | ig. | 2×1,5 | 65 | 28 |
| Example 41 | ig. | 2×150 | 90 | 29 |

| Influence Of Example 34 On The Granuloma Pouch Weight And The Granuloma Pouch Liquid | | | | | |
|---|---|---|---|---|---|
| Substance | Route of administration | dose mg/kg daily | granuloma pouch dry weight % | secretion % | increase in body weight % |
| tragacanth | ig. | | 100 | 100 | 55 |
| Example 34 | ig. | 2×50,0 | 79 | 75 | 51 |
| phenylbutazone | ig. | 2×90,0 | 84 | 96 | 57 |

| Analgesic Effect Of The Substances In The Hot-Plate Test With Mice | | | | | | |
|---|---|---|---|---|---|---|
| Substance | Route of administration | dose mg/kg | influence on the reaction time in % | | | |
| | | | 30' | 60' | 90' | 120' |
| tragacanth | ig. | — | + 15 | + 18 | + 26 | + 15 |
| Example 1 | ig. | 75,0 | + 143 | + 127 | + 48 | + 48 |
| NaCl | sc. | — | + 20 | + 16 | + 20 | + 2 |
| Example 30 | sc. | 125,0 | + 148 | + 140 | + 46 | + 31 |
| NaCl | sc. | — | + 12 | + 22 | + 27 | + 35 |
| Example 31 | sc. | 150,0 | + 51 | + 45 | + 29 | + 18 |
| NaCl | sc. | — | − 2 | − 2 | − 8 | − 8 |
| Example 33 | sc. | 200,0 | + 306 | + 274 | + 244 | + 158 |
| NaCl | sc. | — | − 2 | − 2 | − 8 | − 8 |
| Example 34 | sc. | 100,0 | + 266 | + 202 | + 126 | + 100 |
| tragacanth | ig. | — | + 7 | + 17 | + 29 | + 48 |
| Example 10 | ig. | 250,0 | + 83 | + 77 | + 98 | + 67 |
| tragacanth | ig. | — | + 22 | + 43 | + 37 | + 30 |
| Example 11 | ig. | 200,0 | + 103 | + 102 | + 124 | + 100 |
| tragacanth | ig. | — | + 9 | + 40 | + 49 | + 51 |
| Example 11 | ig. | 250,0 | + 124 | + 154 | + 144 | + 158 |
| tragacanth | ig. | — | + 15 | + 12 | + 17 | + 12 |
| Example 41 | ig. | 200,0 | + 200 | + 250 | + 200 | + 156 |
| tragacanth | ig. | — | + 16 | + 22 | + 10 | + 20 |
| azapropazone | ig. | 500,0 | + 11 | + 5 | + 15 | + 11 |

| Influence On The Normal Body Temperature Of The Rat | | | | | |
|---|---|---|---|---|---|
| Substance | Route of administration | dose mg/kg | change in body temperature after | | |
| | | | 30' | 60' | 120' |
| Example 1 | ig. | 200 | − 1,8 | − 1,8 | − 1,6 |
| Example 30 | ig. | 300 | − 0,6 | − 1,3 | − 1,5 |
| Example 30 | sc. | 300 | − 0,7 | − 0,5 | − 1,0 |
| Example 31 | ig. | 400 | − 0,5 | − 0,4 | + 0,5 |
| Example 31 | sc. | 400 | − 0,5 | − 1,2 | − 0,8 |
| Example 33 | sc. | 400 | − 0,9 | − 1,6 | − 3,2 |
| Example 34 | sc. | 200 | ± 0 | − 1,5 | − 0,3 |
| Example 10 | ig. | 400 | − 2,3 | − 2,2 | − 4,2 |
| Example 11 | ig. | 400 | − 0,8 | − 0,5 | − 0,4 |
| Example 41 | ig. | 400 | − 1,6 | − 1,7 | − 1,9 |
| azapropazone | ig. | 300 | ± 0 | − 0,1 | ± 0 |

Having thus described our invention and the manner and process of making and using it, in such full, clear, concise, and exact terms as to enable any person skilled in the art to which it pertains, or with which it is most nearly connected, to make and use the same.

We claim:

1. Benzo(b)thiophene compounds of the formula:

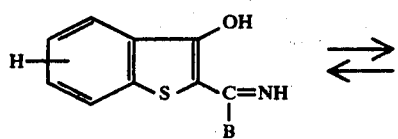 ⇌
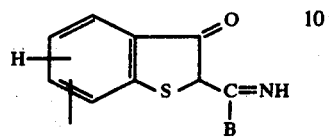
wherein B is selected from the group consisting of:
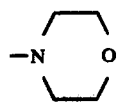
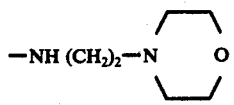
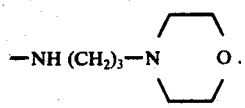
2. The compound of claim 1 wherein B is
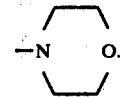
3. The compound of claim 1 wherein B is
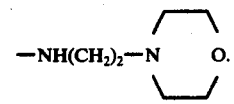
4. The compound of claim 1 wherein B is
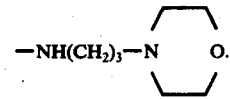
* * * * *